United States Patent [19]

Chabrier de Lassauniere et al.

[11] Patent Number: 5,360,925
[45] Date of Patent: Nov. 1, 1994

[54] DUAL INHIBITORS OF NO SYNTHASE AND CYCLOOXYGENASE, PROCESS FOR THEIR PREPARATION AND THERAPEUTICAL COMPOSITIONS CONTAINING THEM

[75] Inventors: Pierre-Etienne Chabrier de Lassauniere, Paris; Pierre Braquet, Garches; Colette Broquet, Boulogne; Serge Auvin, Saint-Michel-Sur-Orge, all of France

[73] Assignee: Societe de Conseils de Recherches et d'Applications Scientifiques, France

[21] Appl. No.: 128,908

[22] Filed: Sep. 29, 1993

Related U.S. Application Data

[62] Division of Ser. No. 995,792, Dec. 23, 1992.

[30] Foreign Application Priority Data

Jan. 4, 1992 [GB] United Kingdom ............ 9200114.8

[51] Int. Cl.$^5$ ........................................ C07C 229/30
[52] U.S. Cl. ................................................. 560/169
[58] Field of Search ........................................ 560/169

[56] References Cited

U.S. PATENT DOCUMENTS 5,081,148 1/1992 Braquet et al. .................. 514/162

FOREIGN PATENT DOCUMENTS

| 140492 | 5/1985 | European Pat. Off. |
| 424028 | 4/1991 | European Pat. Off. |
| 6838M | 5/1969 | France . |
| 2262529 | 9/1975 | France . |
| 2478092 | 9/1981 | France . |
| 2240041 | 7/1991 | United Kingdom . |
| 9104023 | 4/1991 | WIPO . |

OTHER PUBLICATIONS

Patent Abstracts of Japan, vol. 61, No. 65, Nov. 10, 1980 (Toko Yakuhin Kogyo KK).
Olken et al., "Inactivation of Macrophage Nitric Oxide Synthase Activity by N$^G$-Methyl-L-Arginine", Biochm, Biophys. Res. Commun., vol. 177, No. 2, 1991, pp. 828-833.
Flower et al., "Analgesic-Antipyretics and Anti-Inflammatory Agents", Pharmacological Basis of Therapeutics, Chapter 29, Goodman and Gilman 1985, pp. 674-715.
Patent Abstracts of Japan, vol 12, No. 333 (C-526), Sep. 8, 1988.
Chem. Abstracts, vol. 88, No. 1, Abst. No. 178f, p. 17 Jan. 2, 1978.
H. Tsunematsu et al., "Synthesis and Enzimatic Hydrolysis of Aspirin-Basic Amino Acid Ethyl Esters", International Journal of Pharmaceuticals, vol. 68, No. 1-3, pp. 77-86, Feb. 1, 1991.
W. Armstrong, "Recent trends in research and treatment of stroke", Scrip PJB Publications, 1990, pp. 84-87.
Moncada et al., "Nitric Oxide: Physiology, Pathophysiology and Pharmacology", Pharmacological Reviews 43, 2, 109-142 (1991).
Auget et al., "Comparative effects of endothelin and (List continued on next page.)

Primary Examiner—Mary C. Lee
Assistant Examiner—Joseph K. McKane
Attorney, Agent, or Firm—Lucas & Just

[57] ABSTRACT

The invention relates to compounds of the general formula AB, which may be a salt or an amide, wherein:
A represents a cyclooxygenase inhibitor having an accessible acidic function and
B represents the L-form of arginine analogues of the formula

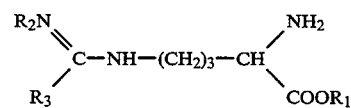

wherein $R_1$, $R_2$ and $R_3$ represent various substituents, process for the preparation of such compounds and pharmaceutical composition thereof.

4 Claims, No Drawings

OTHER PUBLICATIONS phorbol 12-13 dibutyrate in rat aorta", Life Sciences, 1989, 45, 2051–2059.

Auguet et al., "Endothelium independent protective effect of $N^G$-monomethyl-L-arginine on endotoxin-induced alterations of vascular reactivity", Life Sciences, 1991, 48, 189–193.

Auguet et al., "Induction of nitric oxide synthase by lipteichoic acid from Staphylococcus aureus in vascular smooth muscle cells", FEBS vol. 297, Feb. 1992, pp. 183–185.

Chabrier et al., "Regulation of atrial natriuretic factor receptros by Angiotensin II in rat vascular smooth muscle cells", J. Biol. Chem. 1988, 263, 13199–13202.

Cazenave et al., "L'agregation plaquettaire: outil d'investigation clinique et d'etude pharmacologique Metholodoligie", Ann. Biol. Chem. 1983, 41, 167–179.

Green et al., "Analysis of Nitrate, Nitrite and [$^{15}$N]Nitrate in Biological Fluids", Analytical Biochemistry, 126 (1982), 131–138.

Duverger et al., "Systemic administration of a PAF-=antagonist BN 50739, protects against cerebral ischemia", Wissenshaftliscl Verlagsgesellschaft, Stuttgart, 1990, 409–413.

CA 111(19):170013j Topography . . . region, Kulmacz. p. 331, 1989.

CA 117(3):23878r L-NMMA . . . dismutase, Rosenblum et al., p. 447, 1992.

DUAL INHIBITORS OF NO SYNTHASE AND CYCLOOXYGENASE, PROCESS FOR THEIR PREPARATION AND THERAPEUTICAL COMPOSITIONS CONTAINING THEM

This is a division of application Ser. No. 995,792, filed Dec. 23, 1992 pending.

The invention relates to compounds having dual biological activity, a process for their preparation and pharmaceutical compositions containing them. These compounds have dual biological activity, in the sense that they similarly inhibit both the L-Arginine/nitric oxide (NO) pathway and the cyclooxygenase pathway.

Considering the potential role of NO synthase and cyclooxygenase in physiopathology, the compounds may provide effective and favourable benefits in the treatment of:

cardio and cerebrovascular disorders, including, for example, migraine, stroke, infarcts, ischemia, septic, endotoxinic and hemorrhagic shocks, pain;

the various forms of inflammation, including, for example, acute rheumatic fever, rheumatoid arthritis or other types of arthritis, osteoarthrosis, asthma;

immune disorders, including viral or non viral infections, auto-immune diseases, drug abuse, cancer and any pathologies where an excessive production of nitric oxide and/or arachidonic acid metabolites is involved in humans or animals.

Inhibitors of cyclooxygenase or aspirin like drugs, i.e. acetylsalicylic acid and salicylic acid, methylated indole derivatives, such as indomethacin (DCI of 1-(4-chlorobenzoyl)-5-methoxy-2-methyl-1H-indole-3-acetic acid) and sulindac (DCI of 5-fluoro-2-methyl-1-[[4-(methylsulfinyl)phenyl]-methylene]-1H-indene-3-acetic acid), derivatives of N-phenyl-anthranilic acids (meclofenamate, fenamates), propionic acid derivatives such as ibuprofen (DCI of p-isobutylhydratropic acid), naproxen and fenoprofen, are largely employed and have been largely demonstrated, with however some undesirable side effects at high doses, as efficient drug therapy for inflammation (R. Flower, S. Moncada and J. Vane, Mechanism of action of aspirin-like drugs—In the pharmacological basis of therapeutics Goodman and Gilman 1985, 29, 674–715). Moreover, these compounds have been used in both acute and prophylactic treatment of migraine. The value of these drugs is without question although their therapeutic responses are often incomplete and they are not considered to be an adequate treatment by some patients. Considering their anti-inflammatory and platelet anti-aggregant properties, these compounds have also been used in thrombosis and with evidence of a reduction of oedema, in brain ischemia models and hence proposed in the treatment prevention of infarcts, stroke and cerebrovascular diseases (W. Armstrong, Recent trends in research and treatment of stroke. SCRIP, PJB publications. 1991).

Biological activity of inhibitors of nitric oxide synthase has been discovered only recently and their potential therapeutic use is just being considered. These substances, whose structures are represented by L-Arginine analogues and disclosed in U.S. Pat. No. 5,081,148, are inhibitors of nitric oxide (NO) generation. The current knowledge on NO has been exhaustively reviewed in 1991 by Moncada et al, (S. Moncada, R. M. J. Palmer, E. A. Higgs. Nitric oxide: Physiology, Pathophysiology, and Pharmacology. Pharmacological reviews 43, 2, 109–142). Briefly, it appears that NO serves as a transduction mechanism for the soluble guanylate cyclase in vasculature, platelets, nervous system and as an effector molecule in immunological reactions in many cells and tissues, including macrophages or neutrophils. NO is enzymatically generated from L-Arginine by an enzyme called NO synthase. This enzyme exists in two forms: a constitutive one and an inducible one, which are both inhibited by L-Arginine analogues as thereunder defined. In some pathologies, an excessive production of NO may occur, as it has been already demonstrated in shock, as described in the previous cited patent application. In this context, the inhibitors of NO synthase are effective drugs to prevent the vascular consequence and mortality due to the disease, especially when they are combined with inhibitors of cyclooxygenase like aspirin, indomethacin or meclofenamate. Such beneficial effects of the combination of two active principles in the same molecule, is likely to be found in human patients suffering from migraine, stroke, infarcts, cerebral ischemia, pain, inflammations and various immunological diseases. The association of inhibitor of nitric oxyde synthase and inhibitor of cyclooxygenase has been disclosed in the above mentioned patent for the treatment of shock states. However, it has been found that the combination of such compounds provided a better synergic effect than the association.

The invention relates to compounds of the general formula AB which may be a salt or an amide, wherein:

A represents a cyclooxygenase inhibitor having an accessible acidic function, the said cyclooxygenase inhibitor being of the general formula RCOOH wherein COOH stands for the accessible acidic function and R stands for the appropriate radical of the cyclooxygenase inhibitor, and B represents the L-form of arginine analogues of the formula

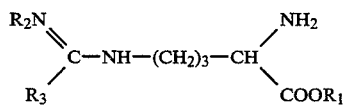

wherein $R_1$ represents a hydrogen atom or a methyl or ethyl group, $R_2$ represents a hydrogen atom or a nitro group and $R_3$ represents an amino, methylamino, ethylamino, hydrazino, methyl or ethyl group with the proviso that if AB is a salt wherein $R_2$ represents a hydrogen atom, then $R_3$ does not represent an amino group.

In a preferred embodiment, the inhibitor of cyclooxygenase of the general formula RCOOH, is selected from within salicylic acid, acetyl salicylic acid, mefenamic acid, ibuprofen, indomethacin and sulindac.

The invention provides also a process for the preparation of compounds, comprising the step of reacting, in substantially equimolar proportions, in the appropriate conditions, a compound A or a precursor of the same wherein A is as above defined, with a compound B or a precursor of the same wherein B is as above defined.

More particularly, the process for the preparation of compounds under the form of a salt of the general formula $$\underset{R_3}{\overset{R_2N}{\diagdown}}C-NH-(CH_2)_3-CH\underset{COOR_1}{\overset{NH_3^+ \quad ^-OCR}{\diagdown}}\overset{\|}{\underset{O}{}}$$

wherein R, $R_1$, $R_2$ and $R_3$ are as above defined, comprises reacting, in water or a mixture of water and alcohol, at a temperature of from room temperature to the boiling point of the reaction mixture, a compound of the general formula A or a precursor of the same wherein A is as above defined, with a compound of the formula B or a precursor of the same wherein B is as above defined. The precursor of the compound A may be a salt of the compound A, such as, for instance, sodium salt. Moreover, the precursor of the compound B may be, for instance, the acetate or the hydrochloride of the compound B. The alcohol used in admixture with water, may be methanol or ethanol.

More particularly, the process for the preparation of compounds under the form of an amide of the general formula $$\underset{R_3}{\overset{R_2N}{\diagdown}}C-NH-(CH_2)_3-CH\underset{COOR_1}{\overset{NH-\overset{O}{\overset{\|}{C}}-R}{\diagdown}}$$

wherein R, $R_1$, $R_2$ and $R_3$ are as above defined, comprises reacting a compound of the general formula B or a precursor of the same, in acetonitrile, at a temperature of from 0° C. to room temperature, in presence of a base, with the precursor of the compound A of the formula RCOX wherein R is as above defined and X stands for a halogene atom. The precursor of the compound B may be, for instance, the hydrochloride of such compound B. The reaction may be carried out in presence of triethylamine as a base.

Finally, the invention provides a pharmaceutical composition comprising an effective amount of compound of the general formula AB, in admixture with a pharmaceutically acceptable diluent or carrier.

The following examples illustrate the invention.

EXAMPLE 1

Compound AB under the salt form, wherein:
A = acetylsalicylic acid
B = N-monomethyl-L-Arginine (L-NMMA)

99 mg (0.52 mmol) of L-NMMA and 95 mg (0.52 mmol) of acetylsalicylic acid were dissolved in 10 ml of ethanol (95%) at room temperature. The stirring was maintained for three hours at room temperature. The solution was concentrated to dryness and the obtained residue was treated with 25 ml of water, then lyophilised to yield 190 mg of the required compound (white solid; m.p. = 170° C.).

$^1$H-NMR (100 MHz, $D_2O$): 7.80–6.60 (m, 4H, aromatic); 3.50 (t, 1H, $CHCO_2H$); 3.10 (m, 2H, $CH_2$—NH); 2.60 (s, 3H, $CH_3$—NH); 2.15 (s, 3H, $CH_3$—CO); 1.90–1.30 (m, 4H, CH—$CH_2$—$CH_2$).

EXAMPLE 2

Compound AB under the salt form, wherein:
A = salicylic acid
B = N-monomethyl-L-Arginine (L-NMMA)

0.52 mmol of N-monomethyl-L-Arginine acetate and 0.52 mmol of sodium salt of salicylic acid were dissolved in water at room temperature. The stirring was maintained at room temperature, until the solution became limpid. The sodium acetate formed was eliminated off and the solution was lyophilised to yield 160 mg of the required compound (white solid; m.p. = 172°–175° C.).

$^1$H-NMR (100 MHz, $D_2O$): 7.75–6.70 (m, 4H, aromatic); 3.55 (t, 1H, CH—COOH); 3.00 (m, 2H, $CH_2$—NH); 2.60 (s, 3H, NH—$CH_3$); 1.90–1.30 (m, 4H, $CH_2$—$CH_2$).

EXAMPLE 3

Compound AB under the salt form, wherein:
A = acetylsalicylic acid
B = N-ω-nitro-L-Arginine (L-NO)

500 mg (2.28 mmol) of N-ω-nitro-L-Arginine and 411 mg (2.28 mmol) of acetylsalicylic acid were dissolved in a mixture of ethanol/$H_2O$ (100 ml/70 ml) in the heat. The stirring was maintained for one hour under reflux. The solution was concentrated to dryness and the obtained residue was treated with 100 ml of water, then lyophilised to yield 900 mg of the required compound (white solid; m.p. > 260° C.).

$^1$H-NMR (100 MHz, $D_2O$): 7.85–6.70 (m, 4H, aromatic); 3.70 (t, 1H, CH—COOH); 3.10 (m, 2H, $CH_2$—NH); 2.16 (s, 3H, $CH_3$); 1.90–1.35 (m, 4H, $CH_2$—$CH_2$).

EXAMPLE 4

Compound AB under the salt form, wherein:
A = salicylic acid
B = N-ω-nitro-L-Arginine (L-NO)

500 mg (2.28 mmol) of N-ω-nitro-L-Arginine and 315 mg (2.28 mmol) of salicylic acid were dissolved in a mixture of ethanol/$H_2O$ (100 ml/70 ml) in the heat. The stirring was maintained for one hour under reflux. The solution was concentrated to dryness and the obtained residue was treated with 100 ml of water, then lyophilised to yield 810 mg of the required compound (white solid; m.p. > 260° C.).

$^1$H-NMR (100 MHz, $D_2O$): 7.78–6.71 (m, 4H, aromatic), 3.53 (t, 1H, CH—COOH), 3.11 (m, 2H, $CH_2$—NH), 2.00–1.30 (m, 4H, $CH_2$—$CH_2$).

EXAMPLE 5

Compound AB under the salt form, wherein:
A = acetylsalicylic acid
B = N-ω-nitro-L-Arginine methyl ester (L-NAME)

This compound has been prepared by mixing, in equimolar proportions, acetyl salicylic acid and N-ω-nitro-L-Arginine methyl ester, according to the method as described in example 3 (yield 98.7%); (white solid; m.p. > 260° C.).

$^1$H-NMR (100 MHz, $D_2O$): 7.8–6.70 (m, 4H, Ph); 3.80 (t, 1H, CH—$CO_2H$); 3.65 (s, 3H, $CO_2CH_3$); 3.10 (m, 2H, $CH_2NH$); 2.11 (s, 3H, $CH_3CO$); 1.90–1.35 (m, 4H, $CH_2$—$CH_2$)

EXAMPLE 6

Compound AB under the salt form, wherein:
A = indomethacin
B = N-ω-nitro-L-Arginine (L-NO)

This compound has been prepared by mixing, in equimolar proportions, indomethacin and N-ω-nitro-L-Arginine according to the method as described in example 3 (yield 97.8%); (white solid; m.p. > 260° C.).

$^1$H-NMR (100 MHz, D$_2$O): 7.70–6.35 (m, 7H, aromatic); 3.95 (m, 1H, CH—COOH); 3.62 (s, 3H, CH$_3$O); 3.35 (s, 2H, CH$_2$—COOH); 3.08 (m, 2H, CH$_2$—NH); 2.10 (2s, 3H, CH$_3$—C≡); 1.72–1.30 (m, 4H, CH$_2$—CH$_2$).

EXAMPLE 7

Compound AB under the salt form, wherein:
A=sulindac
B=N-ω-methyl-L-Arginine (L-NMMA)

This compound has been prepared by mixing, in equimolar proportions, sodium salt of sulindac and N-ω-methyl-L-Arginine acetate, according to the method as described in example 2 (yield 98%); (orange solid, m.p.>260° C.).

$^1$H-NMR (100 MHz, D$_2$O): 7.45 (m, 4H, Ph—SO); 6.95–6.60 (m, 3H, Ph—F); 6.29 (m, 1H, =C—H); 3.15 (m, 5H, CH—COOH, CH$_2$—COOH, CH$_2$NH); 2.72 (s, 3H, CH$_3$—NH); 2.60 (s, 3H, CH$_3$—SO); 1.83 (2s, 3H, CH$_3$—C≡); 1.40 (m, 4H, CH$_2$—CH$_2$).

EXAMPLE 8

Compound AB under the salt form, wherein:
A=ibuprofen
B=N-ω-nitro-L-Arginine (L-NO)

This compound has been prepared by mixing, in equimolar proportions, ibuprofen and N-ω-nitro-L-Arginine, according to the method as described in example 3 (yield 99%); (white solid, m.p.>260° C.).

$^1$H-NMR (100 MHz, D$_2$O): 7 (m, 4H, aromatic); 3.6–3.3 (m, 2H, 2CHCO$_2$H); 3.05 (m, 2H, CH$_2$N); 2.35 (d, 2H, CH$_2$ Ph); 1.8–1.3 (m, 5H, CH$_2$—CH$_2$ and CH(CH$_3$)$_2$); 1.2 (d, 3H, CH—CH$_3$); 0.9 (d, 6H, 2CH$_3$).

EXAMPLE 9

Compound AB under the salt form, wherein:
A=mefenamic acid
B=N-ω-nitro-L-Arginine (L-NO)

This compound has been prepared by mixing, in equimolar proportions, mefenamic acid and N-ω-nitro-L-Arginine, according to the method as described in example 3 (yield 98%); (white solid, m.p.>260° C.).

$^1$H-NMR (100 MHz, CD$_3$OD): 8 (m, 1H, H arom. on o. de CO$_2$H); 7.3–6.5 (m, 6H, aromatic); 3.6 (t, 1H, CHCO$_2$H); 3.3 (m, 2H, CH$_2$NH); 2.2 and 2.3 (2s, 6H, 2CH$_3$); 1.85–1.6 (m, 4H, CH$_2$—CH$_2$).

EXAMPLE 10

Compound AB under the salt form, wherein:
A=indomethacin
B=N-ω-methyl-L-Arginine (L-NMMA)

This compound has been prepared by mixing, in equimolar proportions, sodium salt of indomethacin and N-ω-methyl-L-Arginine acetate, according to the method as described in example 2 (yield 99%); (yellow solid, m.p.>260° C.).

$^1$H-NMR (100 MHz, D$_2$O): 7.70–6.35 (m, 7H, aromatic); 3.67 (2s, 3H, CH$_3$O); 3.47 (m, 1H, CH—COOH); 3.35 (s, 2H, CH$_2$—COOH); 2.97 (m, 2H, CH$_2$—NH); 2.57 (s, 3H, CH$_3$—NH); 2.05 (2s, 3H, CH$_3$—C≡); 1.72–1.30 (m, 4H, CH$_2$—CH$_2$).

EXAMPLE 11

Compound AB under the salt form, wherein:
A=sulindac
B=N-ω-nitro-L-Arginine methyl ester (L-NAME)

This compound has been prepared by mixing, in equimolar proportions, sodium salt of sulindac and N-ω-nitro-L-Arginine methyl ester hydrochloride, according to the method as described in example 2 (yield 98.6%); (orange solid, m.p.>260° C.).

$^1$H-NMR (100 MHz, D$_2$O): 7.30 (m, 4H, Ph—SO); 6.70 (m, 3H, Ph—F); 6.11 (m, 1H, =C—H); 3.78 (m, 1H, CH—COOH); 3.62 (s, 3H, O—CH$_3$); 3.18 (bs, 2H, CH$_2$—COOH); 3.00 (m, 2H, CH$_2$—NH); 2.61 (s, 3H, CH$_3$—SO); 1.83 (bs, 3H, CH$_3$—C≡); 1.90–1.30 (m, 4H, CH$_2$—CH$_2$).

EXAMPLE 12

Compound AB under the salt form, wherein:
A=mefenamic acid
B=N-ω-methyl-L-Arginine (L-NMMA)

This compound has been prepared by mixing, in equimolar proportions, mefenamic acid and N-ω-methyl-L-Arginine, according to the method as described in example 3 (yield 99%); (white solid, m.p.>260° C.).

$^1$H-NMR (100 MHz, CD$_3$OD): 8 (m, 1H, H arom. on o. de CO$_2$H); 7.3–6.5 (m, 6H, Ph); 3.56 (t, 1H, CHCO$_2$H); 3.2 (m, 2H, CH$_2$NH); 2.85 (s, 3H, CH$_3$NH); 2.2 and 2.3 (2s, 6H, 2CH$_3$); 1.8–1.6 (m, 4H, CH$_2$—CH$_2$).

EXAMPLE 13

Compound AB under the salt form, wherein:
A=sulindac
B=N-ω-nitro-L-Arginine (L-NO)

This compound has been prepared by mixing, in equimolar proportions, sulindac and N-ω-nitro-L-Arginine, according to the method as described in example 3 (yield 98%); (orange solid, m.p.>260° C.).

$^1$H-NMR (100 MHz, D$_2$O): 7.30 (m, 4H, Ph—SO); 6.70 (m, 3H, Ph—F); 6.11 (m, 1H, =C—H); 3.78 (m, 1H, CH—COOH); 3.18 (bs, 2H, CH$_2$—COOH); 3.00 (m, 2H, CH$_2$—NH); 2.61 (s, 3H, CH$_3$—SO); 1.83 (bs, 3H, CH$_3$—C≡); 1.90–1.30 (m, 4H, CH$_2$—CH$_2$).

EXAMPLE 14

Compound AB under the salt form, wherein:
A=salicylic acid
B=N-ω-nitro-L-Arginine methyl ester (L-NAME)

This compound has been prepared by mixing, in equimolar proportions, sodium salt of salicylic acid and N-ω-nitro-L-Arginine methyl ester hydrochloride, according to the method as described in example 2 (yield 97.8%); (white solid, m.p.>260° C.).

$^1$H-NMR (100 Mz, D$_2$O): 7.70–6.68 (m, 4H, Ph); 4.00 (t, 1H, CH—COOH); 3.65 (s, 3H, COOCH$_3$); 3.11 (m, 2H, CH$_2$—NH); 2.00–1.30 (m, 4H, CH$_2$—CH$_2$).

EXAMPLE 15

Compound AB under the salt form, wherein:
A=indomethacin
B=N-ω-nitro-L-Arginine methyl ester (L-NAME)

This compound has been prepared by mixing, in equimolar proportions, sodium salt of indomethacin and N-ω-nitro-L-Arginine methyl ester hydrochloride, according to the method as described in example 2 (yield 98.5%); (yellow solid, m.p.>260° C.).

$^1$H-NMR (100 MHz, D$_2$O): 7.70–6.35 (m, 7H, aromatic); 3.95 (m, 1H, CH—COOH); 3.67 (bs, 6H, CH$_3$O, COOCH$_3$); 3.35 (s, 2H, CH$_2$—COOH); 3.08 (m, 2H, CH$_2$—NH); 2.10 (2s, 3H, CH$_3$—C≡); 1.72–1.30 (m, 4H, CH$_2$—CH$_2$).

EXAMPLE 16

Compound AB under the amide form, wherein:
A=acetyl salicylic acid

B = N-ω-nitro-L-Arginine methyl ester (L-NAME)

N-ω-nitro-L-Arginine methyl ester hydrochloride (675 mg, 2.5 mmol) was suspended in anhydrous acetonitrile (15 ml), then 0.7 ml of triethylamine (5 mmol) was added under stirring. The resultant limpid solution was cooled to 0° C. then acetyl salicoyl chloride (0.5 g, 2.5 mmol) in acetonitrile (8 ml) was added and a precipitate formed. The stirring was maintained for two hours at room temperature. Thereafter the precipitate was filtered off and the filtrate concentrated until dryness; the obtained residue was chromatographed on silica column ($CHCl_3$/MeOH 95/5 as eluent), to yield the required compound (73%); (white solid, m.p. = 180° C.).

$^1$H-NMR (100 MHz, $CDCl_3$/$D_2O$): 8.10–6.90 (m, 4H, Ph); 4.85 (m, 1H, CH—COOH); 3.82 (s, 3H, $OCH_3$); 3.40 (m, 2H, $CH_2$—NH); 2.40 (s, 3H, $CH_3$—CO); 2.20–1.50 (m, 4H, $CH_2$—$CH_2$).

EXAMPLE 17

Compound AB under the amide form, wherein:
A = sulindac
B = N-ω-nitro-L-Arginine methyl ester (L-NAME)

This compound has been prepared by using chloride of sulindac and N-ω-nitro-L-Arginine methyl ester, according to the method as described in example 16 (yield 70%); (yellow solid, m.p. = 154°–156° C.).

$^1$H-NMR (100 MHz, $CDCl_3$/$D_2O$): 7.30 (m, 4H, Ph—SO); 6.70 (m, 3H, Ph—F); 6.11 (m, 1H, =C—H); 3.60 (s, 3H, $OCH_3$); 3.15–3.05 (m, 5H, $CH_2CON$, $CHCO_2CH_3$, $CH_2NH$); 2.61 (s, 3H, $CH_3SO$); 2.05 (2s, 3H, $CH_3$—C=); 1.8–1.3 (m, 4H, $CH_2$—$CH_2$).

EXAMPLE 18

Compound AB under the amide form, wherein:
A = ibuprofen
B = N-ω-nitro-L-Arginine methyl ester (L-NAME)

This compound has been prepared by using bromide of ibuprofen and N-ω-nitro-L-Arginine methyl ester according to the method as described in example 16 (yield 78%); (white solid, m.p. = 213° C.).

$^1$H-NMR (100 MHz, $CDCl_3$/$D_2O$): 7 (m, 4H, Ph); 3.6 (s, 3H, $OCH_3$); 3.5–3.3 (m, 2H, CHCON, $CHCO_2CH_3$); 3.10 (t, 2H, $CH_2N$); 2.35 (d, 2H, $CH_2$, Ph); 1.8–1.3 (m, 5H, $CH_2$—$CH_2$, $CH(CH_3)_2$); 1.2 (d, 3H, CH—$CH_3$); 0.8 (d, 6H, $2CH_3$).

The compounds of the invention have been subjected to some biological tests in vitro and in vivo, to prove their activity to block the nitric oxide synthase (constitutive and inducible) and the cyclooxygenase; moreover, the combination is biologically more active than the simple association of the two active principles. Their activity has been also assessed in pathological models in animals; they have been compared with reference substance such as aspirin, indomethacin and L-$N^G$-mono-methyl arginine (L-NMMA), and the simple association of these compounds.

1-In vitro effect on constitutive NO synthase in the isolated rat aorta;

Preparations of isolated rat aorta with endothelium were prepared as previously described (M. Auguet, S. Delaflotte, P. E. Chabrier and P. Braquet—Comparative effects of endothelium and phorbol 12-13 dibutyrate in rat aorta, Life Sciences, 1989, 45, 2051–2059).

Male Sprague Dawley rats (270–360 g, Charles River, Paris) were sacrificed by cervical dislocation and the thoracic aorta removed and cleaned of the surrounding tissue. Rings 2 mm wide were suspended in organ baths containing 10 ml of physiological solution (for composition, see below) under a tension of 2 g at 37° C. and gassed with $O_2$/$CO_2$ (95%/5%). Contractile responses were measured, using force displacement transducers (Slatham $UC_2$) coupled to a Gould 8000 S polygraph. An equilibration period of one hour was allowed before experimentation. Normal physiological solution was composed of (mM): NaCl, 118; KCl, 4.7; $CaCl_2$, 2.5; $KH_2PO_4$, 1.2 ; $MgSO_4$, 0.6; $NaHCO_3$, 25; glucose, 11. After equilibration in normal medium, the preparation was subjected to a near maximal dose (about 95%) of phenylephrine (PE, 1 μM). When the contraction was stable, carbachol (10 μM) was tested in order to evaluate the presence or absence of endothelium.

After washing the preparation and a further reequilibration period of 45 minutes, the preparation was subjected to PE (1 μM) and carbachol (10 μM) was administered to accomplish maximal relaxation. The antagonists were then tested in cumulative-dose-fashion and the $IC_{50}$ (Inhibitory Concentration 50%) to reverse the relaxation of carbachol was calculated. The results are summarised in the following table, paragraph 2-, on the first column of results, entitled "Test on constitutive NO synthase".

2-In vitro effect on inducible NO synthase in the isolated rat aorta:

As previously published (M. Auguet, J. M. Guillon, S. Delaflotte, E. Etiemble, P. E. Chabrier and P. Braquet—Endothelium independent protective effect of $N^G$-monomethyl-L-Arginine on endotoxin-induced alterations of vascular reactivity, Life Sciences, 1991, 48, 189–193), the compounds were tested on isolated rat aorta from shocked animal.

Male Sprague Dawley rats (240–320 g) were intraperitoneally injected with endotoxin (10 mg/kg) or with solvent (saline, 1 mg/kg). Three hours later, endotoxin-treated animals displayed the signs of endotoxemia including piloerection, diarrhea and lethargy. The rats were sacrificed by cervical dislocation and the thoracic aorta removed and cleaned of the surrounding tissue. Rings 2 mm wide were suspended under a tension of 2 g in organ baths containing 10 ml of Krebs-Henseleit solution (mM): NaCl, 118; KCl, 4.7; $CaCl_2$, 2.5; $KH_2PO_4$, 1.2; $MgSO_4$, 1.2; $NaHCO_3$, 25; glucose, 11. This solution was continuously gassed with $O_2$/$CO_2$(95%/5%). The endothelium was mechanically disrupted by gently rolling a small forceps on the luminal surface of the rings. After an equilibration period of 90 minutes, contraction was induced by application of a maximal concentration of phenylephrine (PE, 1 μM). When contraction studies were accomplished, carbachol (10 μM) was tested in order to verify the integrity of endothelium (11). Antagonists were introduced into the bath 45 minutes before application of PE and the $IC_{50}$ was calculated. The results are summarised in the following table, on the second column of results, entitled "Test on inducible NO synthase".

| compounds | Test on constitutive NO synthase $IC_{50}$ (M) | Test on inducible NO synthase $IC_{50}$ (M) |
| --- | --- | --- |
| L-NMMA | $2 \cdot 10^{-5}$ | $2 \cdot 10^{-5}$ |
| aspirin | NA | NA |
| indomethacin | NA | NA |
| example 1 | $10^{-5}$ | $2 \cdot 10^{-5}$ |
| example 2 | $3 \cdot 10^{-6}$ | $9 \cdot 10^{-6}$ |
| example 3 | $6 \cdot 10^{-6}$ | $6 \cdot 10^{-6}$ |
| example 4 | $2 \cdot 10^{-6}$ | $10^{-5}$ |

-continued

| compounds | Test on constitutive NO synthase IC$_{50}$ (M) | Test on inducible NO synthase IC$_{50}$ (M) |
|---|---|---|
| example 5 | $10^{-5}$ | $5 \cdot 10^{-6}$ |
| example 6 | $8 \cdot 10^{-6}$ | $8 \cdot 10^{-6}$ |
| example 8 | $4 \cdot 10^{-6}$ | $10^{-6}$ |
| example 10 | $5 \cdot 10^{-6}$ | $6 \cdot 10^{-6}$ |
| example 12 | $10^{-5}$ | $4 \cdot 10^{-6}$ |
| example 13 | $3 \cdot 10^{-6}$ | $10^{-6}$ |
| example 16 | $9 \cdot 10^{-6}$ | $4 \cdot 10^{-6}$ |
| example 17 | $5 \cdot 10^{-6}$ | $5 \cdot 10^{-6}$ |

NA = Non Active

3-In vitro effect on inducible NO synthase in the lipolysaccharides (LPS) treated vascular smooth muscle cells:

Some of the compounds were also tested on the smooth muscle cells in culture, where the NO synthase was induced by LPS (M. Auguet, M. O. Lonchampt, S. Delaflotte, P. E. Chabrier and P. Braquet—FEBS Letters, 1992, in press).

Smooth muscle cells were isolated by enzymatic (elastase and collagenase) digestion of rat thoracic aorta, as previously described (P. E. Chabrier, P. Roubert, M. O. Lonchampt, P. Plas and P. Braquet—J. Biol. Chem., 1988, 263, 13199-13202). They were cultured for 4 days in DMEM with 10% foetal calf serum and used between passage 3 and 7. Cells monolayers were washed and the medium was replaced with 2 ml of DMEM containing 2 mM glutamine, antibiotics, 0.1 mM isobutylxanthine (IBMX), with or without LPS (*Escherichia Coli*). After 24 hours, cGMP was extracted from cells, by rapid aspiration of the medium and addition of 1 ml of 0.1N HCl to each well. The samples were frozen until cGMP determination, by radioimmunoassay (NEN kit). To study the inhibitory effect, cells were incubated for 24 hours in RPMI 1640 (the concentration of L-arginine was 1.2 mM), with or without LPS (0.1 μg/ml). IBMX (0.1 mM) was added 30 minutes before cGMP extraction, in presence or not of the tested substances ($10^{-4}$M). Diminution of cGMP production was measured (% of diminution) and the obtained results are summarised as follows.

| | diminution of cGMP production (%) |
|---|---|
| control | 0 |
| L-NMMA | 35 |
| example 1 | 30 |
| example 2 | 35 |
| example 3 | 25 |
| example 4 | 25 |
| example 5 | 35 |
| example 6 | 35 |
| example 8 | 25 |
| example 13 | 25 |
| example 17 | 30 |

4-In vitro effect on arachidonic acid induced aggregation of washed rabbit platelets:

This protocol was used to assay the effect of the compounds on the cyclooxygenase. Measurement of platelet aggregation was carried out according to Cazenave et al. (Ann. Biol. Chem. 1983, 41, 167–179). Blood was taken from the auricular artery of male New Zealand rabbit (2.5 kg mean body weight) on ACD (citric acid/sodium citrate/dextrose) as anticoagulant. The washed platelets were prepared and then transferred in the cuvet of the aggregometer (Chronolog aggregometer Coultronics). Additions of the antagonists and arachidonic acid (0.5 mM) were made and percentage of transmission corresponding to aggregation (or its inhibition) was measured, in order to determine the IC$_{50}$. The results are summarised as follows, with the NA abbreviation meaning "non active".

| compounds | IC$_{50}$ (M) |
|---|---|
| aspirin | $2 \cdot 10^{-4}$ |
| indomethacin | $2 \cdot 10^{-5}$ |
| L-NMMA | NA |
| example 1 | $3 \cdot 10^{-4}$ |
| example 2 | $>5 \cdot 10^{-4}$ |
| example 3 | $2 \cdot 10^{-4}$ |
| example 4 | $>5 \cdot 10^{-4}$ |
| example 5 | $5 \cdot 10^{-4}$ |
| example 6 | $4 \cdot 10^{-5}$ |

5-In vitro effect on nitrite production induced by LPS+INFγ on J774 A$_1$ monocyte/macrophage cell line:

Macrophage type cells like J774 A$_1$ cell line are interesting to use since they are important cells in inflammation and express large amount of NO (due to the induction of NO synthase) and cyclooxygenase products. They are activated with lipopolysaccharide (LPS) in presence of interferon γ (INFγ). This assay was used to compare the effects of compounds of the invention with the association of their separated parent compounds.

Murine monocyte/macrophage cells were grown in Dubecco's modified Eagle's medium at 37° C. The cells were plated in 24 well culture plate (NUNC) and were used for experiments at about $2 \times 10^5$ cells/plate. The cells were activated with LPS (1 μg/ml) from *E. Coli* (SO55:B5) and murine recombinant IFNγ (50 U/ml) and then incubated in the presence or absence of the compounds. After 48 h nitrite (NO$_2$−) levels, which correlate with the activation of NO synthase, were assessed in the culture media by the colorimetric method according to Green et al (L. Green, D. Wagner, J. Glogowski, P. Skipper, J. Wishwok and S. Tannenbaum, Analysis of nitrate, nitrite and [15N] nitrate in biological fluids. Analytical Biochemistry 126, 131-138, 1982).

The production of NO$_2$− was undetectable in absence or presence of the compounds when the cells were not activated. In activated cells, the IC$_{50}$ for L-NMMA, L-NO and L-NAME were $8 \times 10^{-6}$M, $1.5 \times 10^{-5}$M and $10^{-3}$M, respectively, whereas the cyclooxygenase inhibitor counterparts salicylic acid, acetyl salicylic acid, indomethacin, meclofenamate were virtually inactive, giving a non significative inhibition between 0.5 to 15%.

To illustrate the more potent activity of the compounds in comparison with the association, some examples are presented in the following table, which presents the percentage of inhibition of nitrite production, induced by LPS+INF on J774 cell line:

| | % OF INHIBITION Concentration (M) | | |
|---|---|---|---|
| Compounds | $10^{-6}$ | $10^{-5}$ | $10^{-4}$ |
| L-NMMA + acetyl salicylic acid | 8% | 27% | 29% |
| Example 1 | 43% | 48% | 67% |
| L-NMMA + salicylic acid | 11% | 29% | 33% |
| Example 2 | 53% | 61% | 75.5% |
| L-NO + acetyl salicylic acid | 2% | 44% | 40% |
| Example 3 | 46% | 49% | 76% |
| L-NMMA + indomethacin | 15% | 34% | 29% |
| Example 10 | 51% | 63% | 66% |
| L-NO + sulindac | 21% | 37% | 40% |

-continued

| Compounds | % OF INHIBITION Concentration (M) | | |
|---|---|---|---|
| | $10^{-6}$ | $10^{-5}$ | $10^{-4}$ |
| Example 13 | 56% | 63% | 71% |
| L-NAME + sulindac | 7% | 24% | 29% |
| Example 17 | 49% | 57% | 73% |

The results show that compounds of the invention are more active, at equivalent concentration, than the association of the separate parent compounds from which they are originated. It indicates also a potentialising effect of the combination of a NO synthase inhibitor and a cyclooxygenase inhibitor.

6-In vitro effect on prostaglandin production induced by LPS+IFNγ on J774A1 monocyte/macrophage cell line:

In the same experiments as above described, we compared the effects of compounds of the invention with the association on the production of cyclooxygenase products, in order to verify whether the enhancement in activity of the compounds is also correlated on the inhibition of cyclooxygenase.

Levels of one of the main cyclooxygenase products produced by J774A1 cell line (i.e.: 6 keto $PGF_{1\alpha}$) the stable metabolite of $PGI_2$ were assessed in the culture media by a specific radioimmunoassay (NEN, Kit NEK 025).

Firstly, it was observed that the release of 6 keto $PGF_{1\alpha}$ in the culture media was not affected by L-NMMA, L-NAME or L-NO but abolished in a dose dependent manner with indomethacin and aspirin with an approximate $IC_{50}$ of $10^{-6}M$ and $10^{-5}M$.

The percentage of inhibition of 6-keto PG F1 production induced by LPS+INF in J774A1 cell line, is presented in the following table, which shows that combinations present a greater activity than the association.

| Compounds | % OF INHIBITION Concentration (M) | | | |
|---|---|---|---|---|
| | $10^{-7}$ | $10^{-6}$ | $10^{-5}$ | $10^{-4}$ |
| L-NO + Acetyl salicylic acid | — | 30% | 58% | 74% |
| Example 3 | — | 58.5% | 78.5% | 91.5% |
| L-NMMA + Indomethacin | 55% | 85% | 84% | — |
| Example 10 | 94% | 97% | 100% | — |
| L-NAME + Sulindac | — | 37% | 48% | 63% |
| Example 17 | — | 74% | 83% | 92% |

7-In vitro effect on nitrite production from murine activated macrophages:

To confirm the results obtained in J774 cell line showing a more potent activity of the synthetized compounds when compared with the association of an inhibitor of cyclooxygenase with an inhibitor of NO synthase, similar experiments were performed on murine activated macrophages.

Peritoneal macrophages were obtained from the peritoneal cavity of femal BBA/2 mice at 7-8 week of age, 3 days after injection of thioglycollate (3% 1.5 ml/mouse). Macrophages ($2.10^5$ cells/well) were activated at 37° C. with LPS (*E. Coli:* 0111B4) (0.1 μg/ml) and murine recombinant INFγ (100 U/ml) in wells of a 96 well-microplate for 20 h on RPMI 1640, 10% FBS, then washed and further incubated for 24 hours. Cells were incubated in absence or presence of the different compounds and nitrite levels were measured in the culture media as already described.

The percentage of the variation compared to the control, is 56% for the combination of indomethacin and L-NMMA (i.e. example 10), 32% for the association of indomethacin and L-NMMA, and less than 30% for each separate compound.

Moreover, the percentage is 48% for the combination of indomethacin and L-NAME (i.e. example 15), 25% for indomethacin, and less than 15% for L-NAME and the association.

8-In vitro effect on lethality induced by NMDA (N-Methyl-D-Aspartate):

Glutamate and aspartate are important neuroexcitotix mediators which are involved in cerebral ischemia. Their actions are notably mediated through the activation of NMDA receptor. IV injection of a high dose of NMDA induced the mortality in mice in less than 35 sec. Any compounds which can delay the time of lethality in this test are considered as potential antiischemic compounds. Since the effects of glutamate or aspartate are possibly mediated by an exaggerated release of NO, we used this test to screen the compounds and to differentiate in vivo the effect of a combination and an association of the separate compounds.

Male OF1 mice (20–22 g, Charles River) were injected with 250 mg/kg NMDA (iv) 1 h after administration by oral route of the substances. Time of survival was measured.

Thus, the combination is much more active than the separate compounds, alone or in association. It also shows a synergism with the combination.

| COMPOUNDS | DOSE (mg/kg IP) | % OF PROTECTION |
|---|---|---|
| Salicylic acid | 4 | — |
| L-NMMA | 5.7 | 6 |
| Salicylic acid + L-NMMA | (4.0 + 5.7) | 6 |
| Example 2 | 10.0 | 66 |
| Salicylic acid | 0.4 | — |
| L-NMMA | 0.57 | 3 |
| Salicylic acid + L-NMMA | (0.4 + 0.57) | 3 |
| Example 2 | 1 | 63 |
| sulindac | 6.4 | 18.2 |
| L-NMMA | 3.4 | 5.4 |
| sulindac + L-NMMA | (6.4 + 3.4) | 20 |
| Example 7 | 10 | 54.5 |
| indomethacin | 6.55 | — |
| L-NMMA | 3.40 | 4.5 |
| indomethacin + L-NMMA | (6.55 + 3.40) | 4.5 |
| Example 10 | 10 | 33.5 |
| Salicylic acid | 3.7 | — |
| L-NAME | 6.3 | 5 |
| Salicylic acid + L-NAME | (3.7 + 6.3) | 5 |
| Example 14 | 10 | 26 |

9-In vivo effect on neuronal death after focal cerebral ischemia in mice:

Systemic intraperitoneal (ip) administration of the compounds was carried out 5 hours after cortical infarction induced by the occlusion of the middle cerebral artery in male Swiss mice (20–22 g), according to Duverger et al.—Pharmacology of cerebral ischemia in Krieglstein and Oberpichler, Wissenschaftliche Verlagsgesellschaft, Stuttgart, 1990, 409–413. Four days later, the mice were decapitated and their brains removed and frozen to be then sectioned in coronal slices of 10 μM thickness. Area infarction was measured by image analysis. Reduction of infarcted volume was measured and compared with non treated animal. The percentage indicated the mean reduction of infarct from six animals per group—MK 801, a NMDA antagonist was used as a control substance. The obtained results are as follows:

|  | Reduction of infarct |
|---|---|
| MK 801 (3 mg/kg) | −51% |
| example 1 (3 mg/kg) | −68% |
| example 2 (3 mg/kg) | −55% |
| example 3 (3 mg/kg) | −70% |
| example 10 (3 mg/kg) | −64% |
| example 17 (3 mg/kg) | −69% |

10-In vivo effect on endotoxin treated pithed rat:

As previously reported, the association of an inhibitor of NO synthase and an inhibitor of cyclooxygenase has a synergistic effect to restore the blood pressure and vascular reactivity in an endotoxinic or septic animal.

Male Sprague Dawley rats (body weight 280–320 g) were pithed. One hour after pithing, animals were given endotoxin (EDTX, *Escherichia Coli*, lipopolysaccharide, O III, $B_4$=300 μg/kg/h) for 60 minutes. This resulted in an important hypotension and a loss of vascular reactivity to vasopressor agents, such as methoxamine. After 60 minutes of perfusion of the compounds with endotoxin, a dose response curve to methoxamine was constructed in a cumulative fashion and an ED50 value (50% of the effective dose to restore normal activity to methoxamine) was determined by regression analysis for each animal. The obtained results are as follows:

| Compounds | Dose mg/kg/h | vascular reactivity to methoxamine $DE_{50}$ (μg/kg) |
|---|---|---|
| control |  | 79 ± 9 |
| EDTX treated animal |  | 278 ± 34 |
| L-NMMA | 50 | 189 ± 15 |
| aspirin | 150 | 136 ± 29 |
| example 1 | 30 | 82 ± 18 |
| example 2 | 30 | 98 ± 35 |
| example 3 | 30 | 76 ± 12 |
| example 4 | 30 | 72 ± 11 |

Toxicology:

Products were administered per os (p.o.) or by intraperitoneal route (i.p.), in groups of 10 mice with increasing doses. $LD_{50}$ (lethal dose 50%) of animals are comprised of from 100 and 1000 per os, and of from 150 and 500 by i.p.

Posology:

The compounds of the invention may be administered at a dose of from 1 to 300 mg per diem.

We claim:

1. Process for the preparation of amide compounds of the formula AB wherein:

A represents a cyclooxygenase inhibitor having an acidic function, the said cyclooxygenase inhibitor being of the formula RCOOH wherein COOH stands for the acidic function and R stands for a radical which corresponds to the radical of the selected cyclooxygenase inhibitor, and B represents the L-form of arginine analogues of the formula

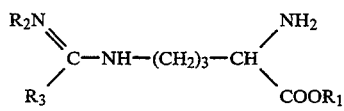

wherein $R_1$ represents a hydrogen atom or a methyl or ethyl group, $R_2$ represents a hydrogen atom or a nitro group and $R_3$ represents an amino, methylamino, ethylamino, hydrazino, methyl or ethyl group, with the proviso that if AB is a salt wherein $R_2$ represents a hydrogen atom, then $R_3$ does not represent an amino group, comprising the step of reacting, in substantially equimolar proportions, in the appropriate conditions, a compound A or a precursor of such a compound A wherein A is as above defined, with a compound B or a precursor of such a compound B wherein B is as above defined.

2. Process according to claim 1, for the preparation of compounds in the form of an amide, the said process comprising reacting a compound of the formula B or a precursor of the same wherein B is as defined in claim 1, in acetonitrile, at a temperature of from 0° C. to room temperature, in presence of a base, with the precursor of the compound A of the formula RCOX wherein A and R are as defined in claim 1 and X stands for a halogen atom.

3. Process for the preparation of amide compounds of the formula AB, wherein:

A represents a cyclooxygenase inhibitor having an acidic function, the said cyclooxygenase inhibitor being selected from the group consisting of salicylic acid, acetyl salicylic acid, mefenamic acid, ibuprofen, indomethacin and sulindac, and B represents the L-form of arginine analogues of the formula

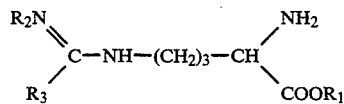

wherein $R_1$ represents a hydrogen atom or a methyl or ethyl group, $R_2$ represents a hydrogen atom or a nitro group and $R_3$ represents an amino, methylamino, ethylamino, hydrazino, methyl or ethyl group, with the proviso that if AB is a salt wherein $R_2$ represents a hydrogen atom, then $R_3$ does not represent an amino group, comprising the step of reacting, in substantially equimolar proportions, in the appropriate conditions, a compound A or a precursor of such a compound A wherein A is as above defined, with a compound B or a precursor of such a compound B wherein B is as above defined.

4. Process according to claim 3, for the preparation of compounds in the form of an amide, the said process comprising reacting a compound of the formula B or a precursor of the same wherein B is as defined in claim 3, in acetonitrile, at a temperature of from 0° C. to room temperature, in presence of a base, with the precursor of the compound A of the formula RCOX wherein A and R are as defined in claim 3 and X stands for a halogen atom.

* * * * *